United States Patent
Yamamoto et al.

(10) Patent No.: US 11,306,013 B2
(45) Date of Patent: Apr. 19, 2022

(54) BIODEGRADATION TREATMENT METHOD FOR ORGANIC COMPOUNDS

(71) Applicant: TAISEI CORPORATION, Tokyo (JP)

(72) Inventors: Norifumi Yamamoto, Tokyo (JP); Yuji Saito, Tokyo (JP); Hironori Taki, Tokyo (JP)

(73) Assignee: TAISEI CORPORATION, Tokyo (JP)

( * ) Notice: Subject to any disclaimer, the term of this patent is extended or adjusted under 35 U.S.C. 154(b) by 187 days.

(21) Appl. No.: 16/622,215

(22) PCT Filed: Jun. 15, 2018

(86) PCT No.: PCT/JP2018/022964
§ 371 (c)(1),
(2) Date: Dec. 12, 2019

(87) PCT Pub. No.: WO2018/235743
PCT Pub. Date: Dec. 27, 2018

(65) Prior Publication Data
US 2020/0180986 A1 Jun. 11, 2020

(30) Foreign Application Priority Data
Jun. 19, 2017 (JP) .............................. JP2017-119725

(51) Int. Cl.
*C02F 3/34* (2006.01)
*C02F 101/34* (2006.01)

(52) U.S. Cl.
CPC .......... *C02F 3/348* (2013.01); *C02F 2101/34* (2013.01)

(58) Field of Classification Search
None
See application file for complete search history.

(56) References Cited

U.S. PATENT DOCUMENTS 5,595,893 A * 1/1997 Pometto, III .......... C12N 11/10
435/136
6,284,523 B1 * 9/2001 Daugulis .................. B09C 1/10
210/600

(Continued)

FOREIGN PATENT DOCUMENTS

CN 102168038 A 8/2011
CN 102433272 A 5/2012

(Continued)

OTHER PUBLICATIONS

"Microbiology Introduction," https://www.sigmaaldrich.com/US/en/technical-documents/technical-article/microbiological-testing/microbial-culture-media-preparation/microbiology-introduction, downloaded Aug. 20, 2021: (Year: 2021).*

(Continued)

*Primary Examiner* — Chester T Barry
(74) *Attorney, Agent, or Firm* — Law Office of Katsuhiro Arai

(57) ABSTRACT

An object is to provide an efficient treatment method for organic compounds using constitutive 1,4-dioxane-degrading bacterium strain N23. As a means for achieving the object, a biodegradation treatment method is provided, wherein organic compounds are biodegradation-treated with strain N23, which is a constitutive 1,4-dioxane-degrading bacterium deposited under Accession No. NITE BP-02032, under a condition of pH 3.0 or higher but no higher than 5.5.

10 Claims, 5 Drawing Sheets

(56) References Cited

U.S. PATENT DOCUMENTS

| | | | |
|---|---|---|---|
| 2014/0357523 A1* | 12/2014 | Zeiner | C12N 15/1003 506/11 |
| 2015/0337344 A1 | 11/2015 | Albuquerque et al. | |
| 2016/0326031 A1 | 11/2016 | Amy et al. | |
| 2018/0135141 A1 | 5/2018 | Yamamoto et al. | |

FOREIGN PATENT DOCUMENTS

| | | | |
|---|---|---|---|
| JP | 2008306939 A | 12/2008 | |
| JP | 2013179897 A | 9/2013 | |
| JP | 2016504911 A | 2/2016 | |
| JP | 5877918 B1 | 3/2016 | |
| JP | 2016077284 A | 5/2016 | |
| JP | 2017042097 A | 3/2017 | |
| JP | 6117450 B1 | 4/2017 | |
| WO | 2014102297 A1 | 7/2014 | |
| WO | 2016181802 A1 | 11/2016 | |

OTHER PUBLICATIONS

Extended European Search Report (EESR) dated Feb. 18, 2021, issued for European counterpart patent application No. EP18819732.1 (8 pages).

Adams et al., Oxidation and biodegradability enhancement of 1,4-dioxane using hydrogen peroxide and ozone, Environ. Sci. Technol., 1994, pp. 1812-1818, 28(11) (7 pages).

Imaeda et al., Microbiological degradation of LLC, Toyota Central R&D Labs,1999, p. 23-30, vol. 34, No. 3 (8 pages).

International Search Report (ISR) dated Sep. 4, 2018, issued for International application No. PCT/JP2018/022964. (2 pages).

Kosaka et al., The effects of the co-existing compounds on the decomposition of micropollutants using the ozone/hydrogen peroxide process, Water Sci.Technol., 2000, pp. 353-361, vol. 42 (9 pages).

Sei et al., Challenge for biotreatment of groundwater contaminated with 1,4-dioxane by 1,4-dioxane-degrading bacteria, J. Water and Waste water, 2011, pp. 555-560, vol. 53, No. 7 (4 pages).

Sei et al., Isolation and characterization of bacterial strains that have high ability to degrade 1,4-dioxane as a sole carbon and energy source, Biodegradation, 2012, p. 665-674, vol. 24, No. 5 (10 pages).

International Preliminary Report on Patentability, dated Dec. 24, 2019, for corresponding international application PCT/JP2018/022964 (1 page).

Notification Concerning Transmittal of International Preliminary Report on Patentability, dated Jan. 2, 2020, for corresponding international application PCT/JP2018/022964 (1 page).

Notification of Transmittal of Translation of the International Preliminary Report on Patentability, dated Jan. 2, 2020, for corresponding international application PCT/JP2018/022964 (1 page).

Written Opinion of the International Searching Authority, dated Sep. 4, 2018, for corresponding international application PCT/JP2018/022964 (6 page).

* cited by examiner

[FIG. 1]
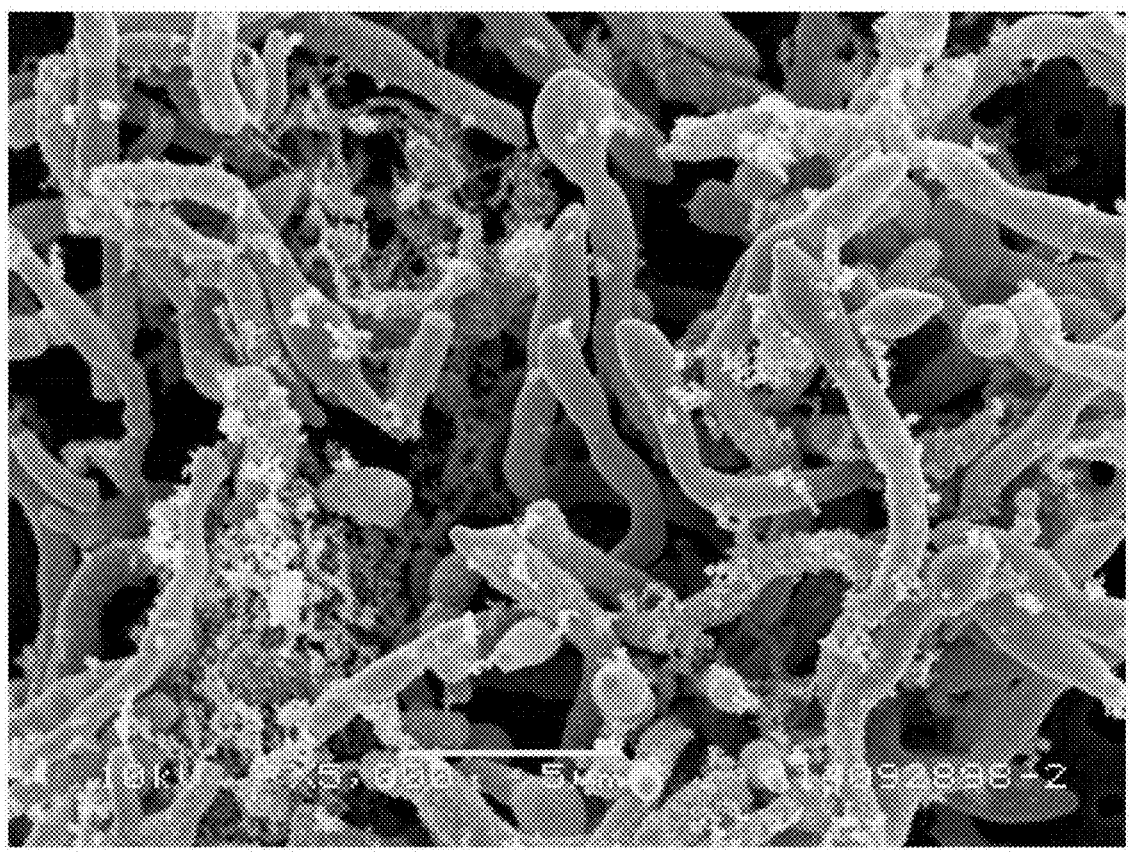

[FIG. 2]
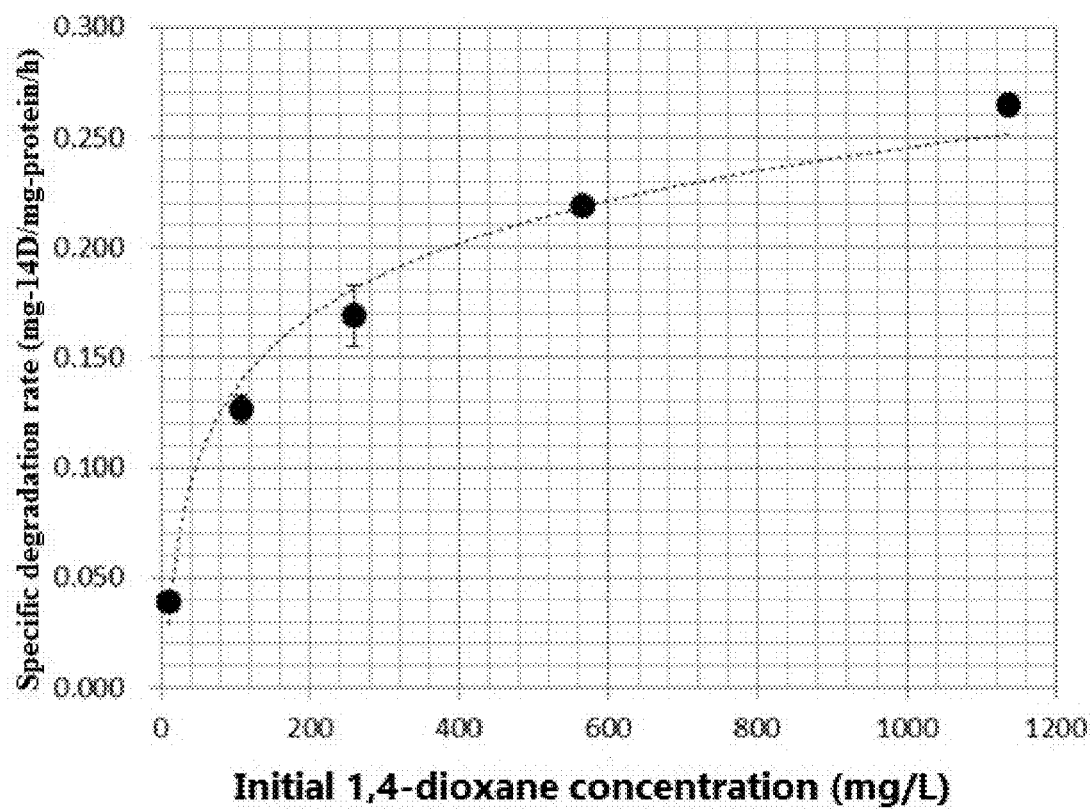

[FIG. 3]
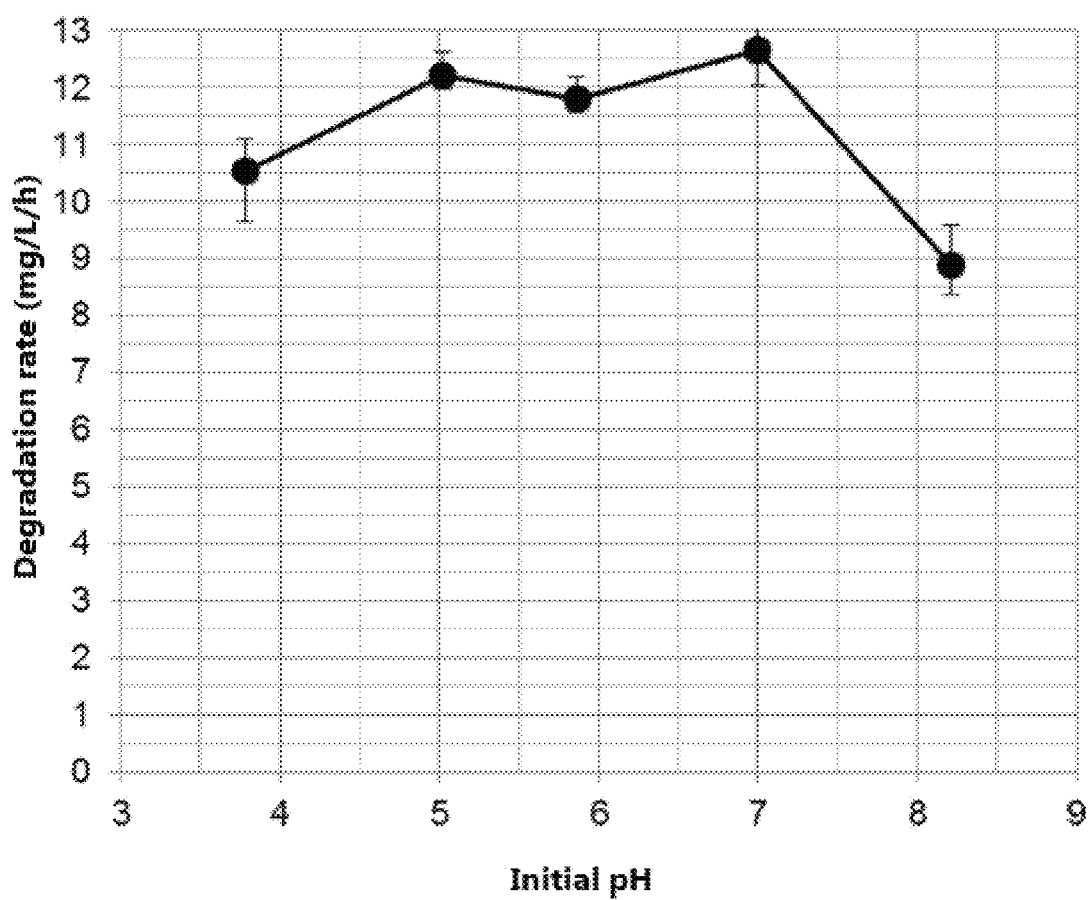

[FIG. 4]
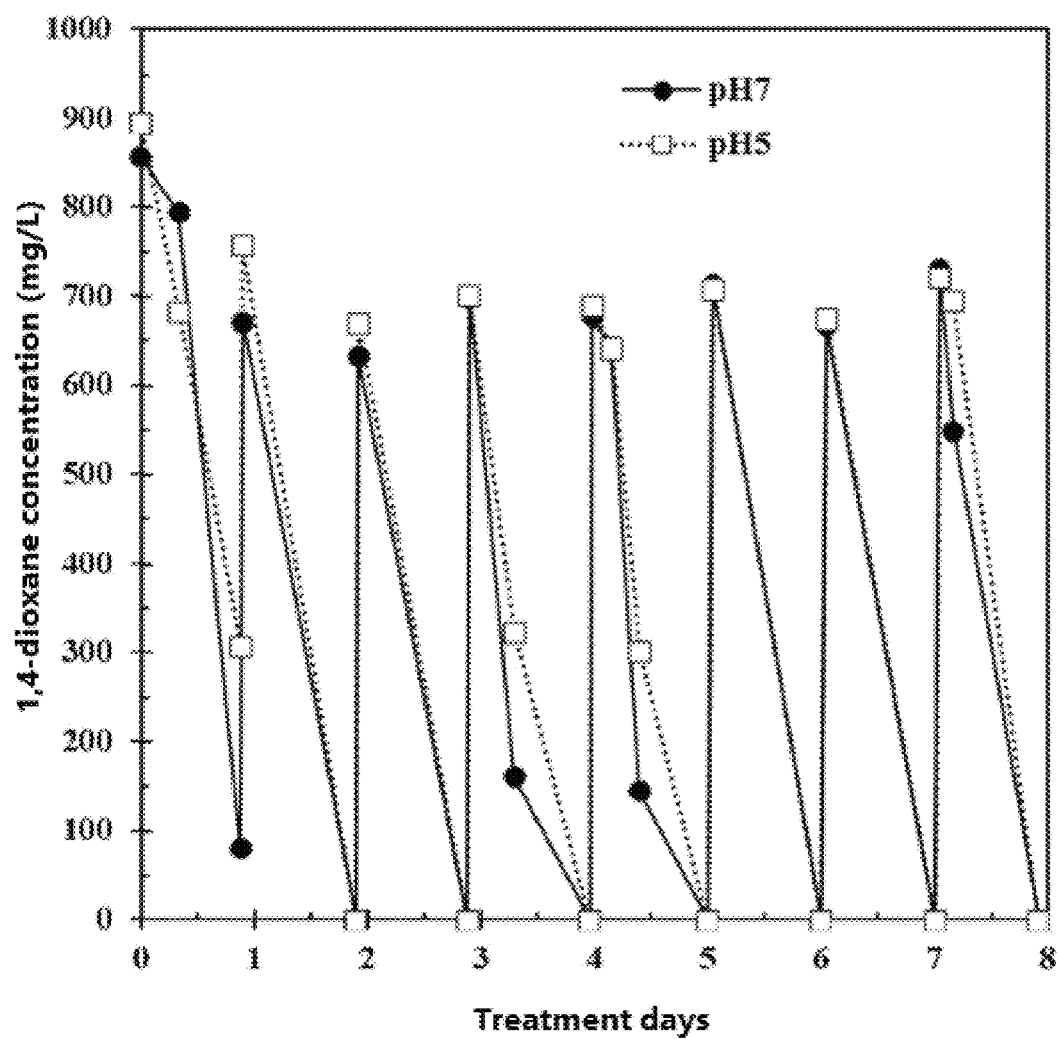

[FIG. 5]
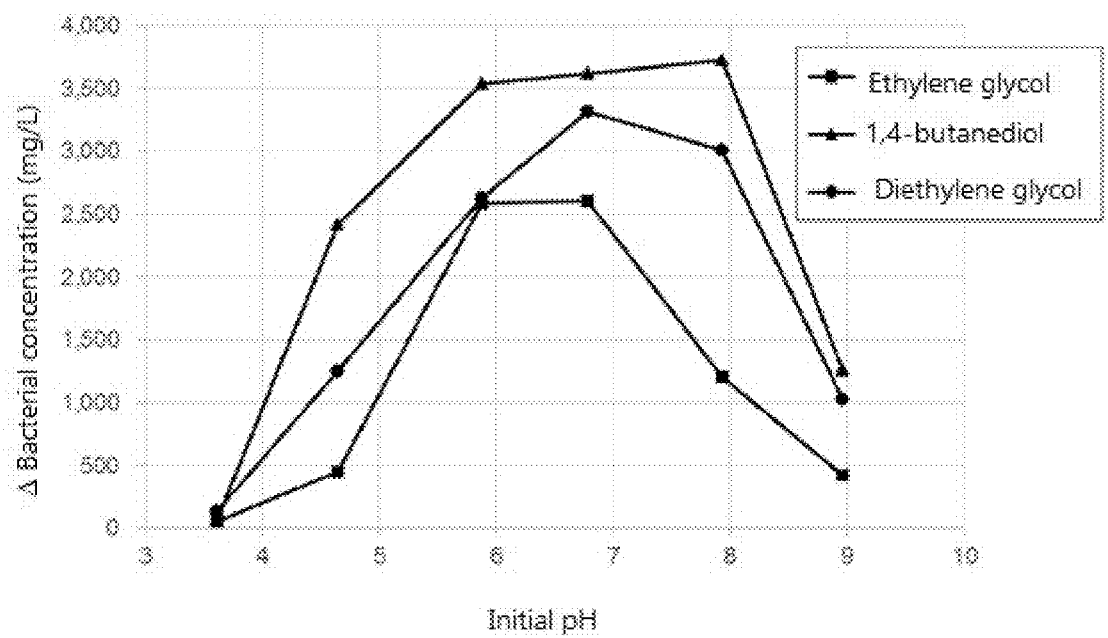

BIODEGRADATION TREATMENT METHOD FOR ORGANIC COMPOUNDS

CROSS-REFERENCE TO RELATED APPLICATIONS

This application is the U.S. National Phase under 35 U.S.C. § 371 of International Application PCT/JP2018/022964, filed Jun. 15, 2018, which claims priority to Japanese Patent Application No. JP2017-119725, filed Jun. 19, 2017. The International Application was published under PCT Article 21(2) in a language other than English.

TECHNICAL FIELD

The present invention relates to a biodegradation treatment method for organic compounds utilizing constitutive 1,4-dioxane-degrading bacterium strain N23.

BACKGROUND ART 1,4-dioxane is a cyclic ether expressed by Formula (1) below. 1,4-dioxane has excellent compatibility with water and organic solvents and is primarily used as a reaction solvent in organic synthesis.

[Chem 1]

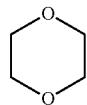

(1)

Approx. 4,500 tons of 1,4-dioxane was manufactured in or imported to Japan in 2010, while approx. 300 tons is estimated to have been released to the environment during the year. 1,4-dioxane is soluble in water, which means that it will spread over wide areas once released to a water environment. In addition, 1,4-dioxane is low in volatility, solid absorptivity, photodegradability, hydrolyzability and biodegradability, which makes it difficult to remove 1,4-dioxane from water. Because 1,4-dioxane has acute toxicity and chronic toxicity and has been identified as a carcinogen, there are concerns that 1,4-dioxane pollution in water environments will have adverse effects on humans, animals, and plants. For these reasons, Japan regulates 1,4-dioxane by setting a tap water quality standard (0.05 mg/L or less), an environmental standard (0.05 mg/L or less), and a wastewater standard (0.5 mg/L or less).

Also, it is reported in Non-patent Literature 1 that industrial effluent containing 1,4-dioxane also contains cyclic ethers such as 1,3-dioxolane and 2-methyl-1,3-dioxolane in addition to 1,4-dioxane. In particular, 1,3-dioxolane has been confirmed to have acute toxicity and other toxic properties, and therefore contaminated water containing 1,3-dioxolane must be treated properly.

Conventional treatment methods, such as the activated sludge method and the active carbon absorption method, cannot remove 1,4-dioxane and other cyclic ethers completely from water. For example, only the advanced oxidation processes that combine multiple physiochemical oxidation methods, such as ozone treatment with added hydrogen peroxide ($O_3/H_2O_2$), ozone treatment under ultraviolet irradiation ($O_3/UV$), and ozone treatment under radiation exposure or ultrasonic irradiation, have been confirmed effective in treating 1,4-dioxane. However, the advanced oxidation processes require high initial cost and running cost and are therefore not yet popular. Also, it is reported in Non-patent Literature 2 that presence of organic substances other than 1,4-dioxane causes the efficiency of 1,4-dioxane treatment under the advanced oxidation processes to drop.

Methods are being sought for treating water containing 1,4-dioxane and other cyclic ethers at low cost and in a stable manner, and Patent Literature 1 and Non-patent Literature 3 propose treating 1,4-dioxane using 1,4-dioxane-degrading bacteria. 1,4-dioxane-degrading bacteria are largely classified into two groups: bacteria that degrade 1,4-dioxane as a single carbon source (assimilating bacteria); and bacteria that can degrade 1,4-dioxane in the presence of tetrahydrofuran or other specific matrix (co-metabolic bacteria). To treat 1,4-dioxane contained in groundwater, wastewater, etc., using 1,4-dioxane-degrading bacteria, therefore, it is efficient to use assimilating bacteria that do not require any specific matrix to be added.

Assimilating bacteria are further classified into inducible types and constitutive types based on whether or not a 1,4-dioxane-degrading enzyme is induced. As described in Non-patent Literature 4, inducible 1,4-dioxane-degrading bacteria produce/secrete a degrading enzyme in the presence of 1,4-dioxane or other inducing substance and must therefore be acclimated before they can be used in 1,4-dioxane treatment. On the other hand, constitutive 1,4-dioxane-degrading bacteria are constantly producing a degrading enzyme and can therefore be used in 1,4-dioxane treatment immediately without acclimation.

Now, 1,4-dioxane-degrading bacteria are extremely slow to grow, which means that, if any other microorganism has intermixed, that other microorganism will grow preferentially. For this reason, culturing 1,4-dioxane-degrading bacteria requires fully sterilizing the culture apparatus and culture medium beforehand in order to prevent other microorganisms from intermixing. Methods for sterilization treatment include steam sterilization using an autoclave, dry heat sterilization involving heating in an oven, etc., radiation sterilization using gamma rays, and chemical sterilization using ethylene oxide gas, or the like. However, it is difficult to conduct any of these sterilization methods on a large scale for reasons such as: requiring too large a facility for sterilization; incurring too much energy cost; and presenting cost/safety problems stemming from use of large quantities of chemicals.

The inventors of the present application for patent proposed, in Patent Literature 2, a culture method for 1,4-dioxane-degrading bacteria that uses a culture medium containing diethylene glycol to increase 1,4-dioxane-degrading bacteria. Compared to other microorganisms, 1,4-dioxane-degrading bacteria have an excellent ability to utilize diethylene glycol as a carbon source, and therefore use of a medium containing diethylene glycol allows 1,4-dioxane-degrading bacteria to grow preferentially without sterilization, even under a condition of cohabitation with other microorganisms.

Furthermore, the inventors of the present invention reported, in Patent Literature 3, strain N23 which is a constitutive 1,4-dioxane-degrading bacterium. Strain N23 exhibits the highest 1,4-dioxane maximum specific degradation rate among the constitutive 1,4-dioxane-degrading bacteria that have been reported so far, and is very promising in the biodegradation of cyclic ethers such as 1,4-dioxane.

Compared to microorganisms having no 1,4-dioxane degrading capability, strain N23 has an excellent ability to utilize 1,4-dioxane, ethylene glycol, diethylene glycol, and 1,4-butanediol as carbon sources. Also, it has been reported that, among the aforementioned organic substances that can be easily utilized by strain N23 as carbon sources, ethylene glycol is hardly biodegraded in an acidic environment of pH 5.0 or lower (Non-patent Literature 5).

BACKGROUND ART LITERATURE

Patent Literature

Patent Literature 1: Japanese Patent Laid-open No. 2008-306939
Patent Literature 2: Japanese Patent No. 5877918
Patent Literature 3: Japanese Patent No. 6117450

Non-Patent Literature

Non-patent Literature 1: CD. Adams, Pa. Scanlan and ND. Secrist: Oxidation and biodegradability enhancement of 1,4-dioxane using hydrogen peroxide and ozone, Environ. Sci. Technol., 28 (11), pp. 1812-1818, 1994.
Non-patent Literature 2: K. Kosaka, H. Yamada, S. Matsui and K. Shishida: The effects of the co-existing compounds on the decomposition of micropollutants using the ozone/hydrogen peroxide process, Water Sci. Technol., 42, pp. 353-361, 2000.
Non-patent Literature 3: Kazunari Sei and Michihiko Ike: Challenge for biotreatment of groundwater contaminated with 1,4-dioxane by 1,4-dioxane-degrading bacteria, J. Water and Waste water, Vol. 53, No. 7, pp. 555-560, 2011.
Non-patent Literature 4: K. Sei, K. Miyagaki, T. Kakinoki, K. Fukugasako, D. Inoue and M. Ike: Isolation and characterization of bacteria strains that have high ability to degrade 1,4-dioxane as a sole carbon and energy source, Biodegradation, 24, 5, pp. 665-674, 2012.
Non-patent Literature 5: Takao Imaeda, Kenro Tokuhiro and Masana Hirai: Microbiological degradation of LLC, Toyota Central R&D Labs, Vol. 34, No. 3, pp. 23-30, 1999.

SUMMARY OF THE INVENTION

Problems to be Solved by the Invention

An object of the present invention is to provide an efficient treatment method for organic compounds using constitutive 1,4-dioxane-degrading bacterium strain N23.

Means for Solving the Problems

1. A biodegradation treatment method characterized in that organic compounds are biodegradation-treated with strain N23, which is a constitutive 1,4-dioxane-degrading bacterium deposited under Accession No. NITE BP-02032, under a condition of pH 3.0 or higher but no higher than 5.5.
2. A biodegradation treatment method according to 1, characterized in that the organic compounds include cyclic ethers.
3. A biodegradation treatment method according to 1 or 2, characterized in that the organic compounds include at least one type of substance selected from 1,4-dioxane, 1,3-dioxolane, 2-methyl-1,3-dioxolane and tetrahydrofuran.
4. A biodegradation treatment method according to any one of 1 to 3, characterized in that at least one type of substance selected from ethylene glycol, diethylene glycol, 1,4-butanediol, and 1,4-dioxane is added as a carbon source.
5. A biodegradation treatment method according to 1, characterized in that the organic compounds include at least one type of substance selected from ethylene glycol, diethylene glycol, and 1,4-butanediol.
6. A biodegradation treatment method according to any one of 1 to 5, characterized in that it is a fed-batch process.
7. A biodegradation treatment method according to any one of 1 to 5, characterized in that it is a continuous process.

Effects of the Invention

In an acidic environment of pH 3.0 or higher but no higher than 5.5, actions of other microorganisms are suppressed, but activities of strain N23 barely drop. For this reason, the biodegradation treatment of organic compounds by strain N23 can be performed efficiently in an acidic environment of pH 3.0 or higher but no higher than 5.5. Strain N23 is a constitutive 1,4-dioxane-degrading bacterium and constantly produces a degrading enzyme. Strain N23 can degrade cyclic ethers without acclimation, induction, etc., thus allowing for efficient treatment of cyclic ethers. Additionally, strain N23 can also be used in the biodegradation treatment of ethylene glycol, diethylene glycol, and 1,4-butanediol. As it can be active over a wide acid range of pH 3.0 or higher but no higher than 5.5, strain N23 does not require strict adjustment of pH at the time of treatment and thus can be managed with ease.

When treating an organic compound of high concentration, strain N23 acts by using the target organic compound as a carbon source, thus enabling its biodegradation treatment. When treating an organic compound of low concentration, the bacterial concentration of strain N23 can be maintained at a high level by adding at least one type of substance selected from ethylene glycol, diethylene glycol, 1,4-butanediol, and 1,4-dioxane as a carbon source, which allows for an efficient biodegradation treatment of the organic compound.

When contaminated water is treated through a fed-batch process, the quantity of strain N23 increases every time the process is repeated, which allows the time needed to complete one process cycle to be shortened gradually. Additionally, in a fed-batch process, the initial contaminant concentration is high and therefore the degradation activity from strain N23 can be maintained at a high level, which means that the contaminant can be degraded over a short period of time. Treating contaminated water through a continuous process ensures low cost because an existing purification facility can be used without modification, while also allowing a biodegradation treatment process to be built quickly and easily.

BRIEF DESCRIPTION OF THE DRAWINGS

FIG. 1 An SEM image of strain N23.
FIG. 2 A diagram showing the specific degradation rate of 1,4-dioxane by strain N23 relative to the initial concentration of 1,4-dioxane.
FIG. 3 A diagram showing the relationship of initial pH and cyclic ether degradation rate in Experiment 1.
FIG. 4 A diagram showing how the 1,4-dioxane concentrations change over time in Example 1 and Comparative Example 1 of Experiment 2.
FIG. 5 A diagram showing the relationships of initial pH and amount of increase in bacterial concentration with different carbon sources in Experiment 3.

MODE FOR CARRYING OUT THE INVENTION

The present invention is explained in detail below.
(Strain N23)
The constitutive 1,4-dioxane-degrading bacterium strain N23 (hereinafter referred to as "strain N23") used in the present invention has been internationally deposited, effective Apr. 10, 2015, with the National Institute of Technology and Evaluation's Patent Microorganisms Depositary (NPMD) (2-5-8 Kazusakamatari, Kisarazu-shi, Chiba, Japan (Postal Code 292-0818)) under Accession No. NITE BP-02032. An SEM image of strain N23 is shown in FIG. 1. Strain N23 is Gram-positive and catalase-positive.

Strain N23 is a constitutive 1,4-dioxane-degrading bacterium and constantly producing a degrading enzyme. In general, constitutive 1,4-dioxane-degrading bacteria are known to exhibit lower 1,4-dioxane maximum specific degradation rates compared to inducible 1,4-dioxane-degrading bacteria. The specific degradation rate of 1,4-dioxane by strain N23 relative to the initial concentration of 1,4-dioxane is shown in FIG. 2.

Strain N23 has the highest 1,4-dioxane maximum specific degradation rate among the constitutive 1,4-dioxane-degrading bacteria that have been reported so far, and this value is equal to or higher than those of inducible 1,4-dioxane-degrading bacteria. Also, strain N23 can degrade 1,4-dioxane to extremely low concentrations of 0.017 mg/L or lower, and is capable of treating 1,4-dioxane of such high concentrations as approx. 5200 mg/L.

Strain N23 need not be acclimated beforehand using 1,4-dioxane, etc. Also, strain N23 has a high 1,4-dioxane maximum specific degradation rate, and is capable of degrading 1,4-dioxane to extremely low concentrations and treating 1,4-dioxane of high concentrations. Accordingly, strain N23 can be utilized favorably in the treatment of 1,4-dioxane.

Strain N23 can efficiently degrade 1,3-dioxolane, 2-methyl-1,3-dioxolane, tetrahydrofuran, and other cyclic ethers, in addition to 1,4-dioxane. It can also treat multiple cyclic ethers simultaneously. Furthermore, strain N23 has excellent ethylene glycol, diethylene glycol, and 1,4-butanediol degradability. Accordingly, strain N23 can be utilized favorably in the biodegradation treatment of cyclic ethers such as 1,4-dioxane, 1,3-dioxolane, 2-methyl-1,3-dioxolane, and tetrahydrofuran, as well as ethylene glycol, diethylene glycol, and 1,4-butanediol.

Strain N23 presents little drop in activity, even in an acidic environment of pH 3.0 or higher but no higher than 5.5. To be specific, while strain N23 exhibits the highest 1,4-dioxane degradation activity near pH 7.0, it maintains degradation activity of 90% or greater at pH 5.0, and 80% or greater at pH 3.8, relative to the degradation activity at pH 7.0. In contrast, a neutral environment of approx. pH 6.0 to 8.0 is an optimum pH for many microorganisms. For example, among the organic substances that can be proficiently utilized by strain N23 as carbon sources, ethylene glycol has been reported to have an optimum biodegradation pH in a neutral environment (pH 6 to 8) and remain barely biodegraded in an acidic environment of pH 5.0 or lower (Non-patent Literature 5). Meanwhile, no dioxane-degrading bacterium has been reported so far that demonstrates high 1,4-dioxane degradation activity in an acidic environment; for example, strain D17 (Accession No. NITE BP-01927), which is a constitutive 1,4-dioxane-degrading bacterium, exhibits the highest degradation activity at pH 8.0 and its degradation activity at pH 5.0 is only around 50% of the degradation activity at pH 8.0 (Non-patent Literature 4).

(Biodegradation Treatment Method)

The biodegradation treatment method proposed by the present invention is characterized in that organic compounds are biodegradation-treated with strain N23 in an acidic environment of pH 3.0 or higher but no higher than 5.5.

The target of biodegradation treatment includes ground water, contaminated water such as factory effluent, and contaminated soil at illegal damping sites, etc., which contain organic compounds. Various types of microorganisms (hereinafter referred to as "saprophytes") live in contaminated water, contaminated soil, etc. As described above, general saprophytes have an optimum pH in a neutral environment, which means that actions of saprophytes are suppressed in an acidic environment of pH 3.0 or higher but no higher than 5.5. In an acidic environment of pH 3.0 or higher but no higher than 5.5, where actions/growth of saprophytes are suppressed and strain N23 acts preferentially, the biodegradation treatment of organic compounds by strain N23 can be performed efficiently. It should be noted that, because the biodegradation treatment proposed by the present invention is performed in an acidic environment, the environment must be returned to neutral after the biodegradation treatment. Since the soil neutralization process requires a large-scale facility, it is desirable that, even when the contaminated soil is purified, the soil is washed with water beforehand and the organic compound to be treated is transitioned to the water phase so that contaminated water will be treated.

The method for biodegrading organic compounds in contaminated water using strain N23 is not limited in any way, but it may be implemented through, for example: a so-called fed-batch process where (1) a biodegradation treatment step for contaminated water with strain N23, (2) a water discharge step to precipitate activated sludge, carrier, etc. containing strain N23 and then discharge the supernatant water after treatment, and (3) a contaminated-water introduction step to introduce new contaminated water, are repeated in the order of (1)→(2)→(3)→(1)→ . . . ; or a continuous process where introduction of contaminated water upstream and discharge of treated water downstream are performed continuously by equal quantities. A fed-batch process allows the biodegradation treatment rate to be maintained at a high level because the initial contaminant concentration in the aeration tank is high. Also, hardly any strain N23 flows out during water discharge and the amount of strain N23 increases every time the process is repeated, which means that the time needed to complete one process cycle can be shortened gradually. In a continuous process, an existing wastewater treatment facility can be used without modification.

The organic compounds to be biodegradation-treated are not limited in any way so long as they can be degraded, or specifically utilized as a carbon source, by strain N23. For example, they include cyclic ethers such as 1,4-dioxane, 1,3-dioxolane, 2-methyl-1,3-dioxolane, and tetrahydrofuran, as well as ethylene glycol, diethylene glycol, and 1,4-butanediol. Among the above, cyclic ethers are particularly preferred because strain N23 is constantly secreting an enzyme to degrade them.

An example of contaminated water is explained below.

If the organic compound to be treated (hereinafter referred to as "treating organic compound") in the contaminated water has a high concentration, strain N23 can utilize the treating organic compound in the contaminated water as a carbon source to efficiently treat it for biodegradation while maintaining the bacterial mass.

If the concentration of the treating organic compound in the contaminated water is low, the bacterial concentration of strain N23 may become low and the efficiency of biodegradation treatment may drop. If the concentration of the treating organic compound is low, therefore, it is desirable that at least one type of substance selected from ethylene glycol, diethylene glycol, 1,4-butanediol, and 1,4-dioxane is added to the contaminated water as a carbon source. Any one of the foregoing may be added alone, or two or more may be mixed and added. Among these, ethylene glycol is preferred for reasons such as: utilization of saprophytes is difficult and saprophyte propagation is suppressed in an acidic environment; and even if the substance flows out, it will be biodegraded quickly in a neutral environment.

Strain N23 can grow, under acidic conditions, by using ethylene glycol, diethylene glycol, 1,4-butanediol, and 1,4-dioxane as carbon sources. This means that, even when the concentration of the treating organic compound is low, the bacterial concentration of strain N23 can be maintained at a high level by adding at least one type selected therefrom to the contaminated water as a carbon source, in which case the treatment of the low-concentration treating organic compound by strain N23 can be performed efficiently. As a rough guide for adding a carbon source to the contaminated water, the concentration of the treating organic compound is approx. 400 mg/L or lower. Also, the total concentration of the carbon sources to be added to the contaminated water is preferably 10 mg/L or higher but no higher than 100 g/L, or more preferably 100 mg/L or higher but no higher than 10 g/L, or yet more preferably 200 mg/L or higher but no higher than 5 g/L.

(Culture Method)

Preferably strain N23 used for biodegradation treatment is cultured in an acidic environment of pH 3.0 or higher but no higher than 5.5. In an acidic environment of pH 3.0 or higher but no higher than 5.5, saprophyte propagation is suppressed and therefore strain N23 can be cultured efficiently. In the interest of more reliably preventing saprophyte contamination, the pH during culturing is preferably low, or more preferably pH 4.9 or lower, or yet more preferably pH 4.5 or lower.

The culture medium in which to culture strain N23 may be a liquid culture medium or solid culture medium. The culture medium is not limited in any way so long as strain N23 can be cultured in it, and any known culture medium such as MGY culture medium or CGY culture medium may be used. So that a large quantity of strain N23 can be cultured, preferably a liquid culture medium is used. More preferably continuous culture is performed, where a liquid culture medium is supplied, while a cultured broth containing strain N23 is taken out by the same quantity as the supplied quantity of liquid culture medium.

In an acidic environment, where actions/growth of saprophytes are suppressed, strain N23 can be cultured without implementing a complete sterilization treatment before culturing. Also, strain N23 can be cultured in an acidic environment using a large-capacity culture apparatus that presents difficulty in disinfecting every corner without fail, because saprophyte contamination is unlikely. To be specific, the capacity of the culture tank may be 10 L or greater but no greater than 1000 L when culturing strain N23 using a liquid culture medium in an acidic environment.

EXAMPLES (Strain N23)

Strain N23 was cultured for two weeks using an MGY culture medium (composition: 10 g/L of malt extract, 4 g/L of glucose, 4 g/L of yeast extract; pH 7.3). This culture broth was harvested through 3 minutes of centrifuging at 10000×g and 4° C., followed by washing, twice, using an inorganic salt culture medium (composition of culture medium: 1 g/L of $K_2HPO_4$, 1 g/L of $(NH_4)_2SO_4$, 50 mg/L of NaCl, 200 mg/L of $MgSO_4.7H_2O$, 10 mg/L of $FeCl_3$, 50 mg/L of $CaCl_2$); pH: 7.3), and the resulting bacteria were used.

Experiment 1

Effects of pH on Cyclic Ether Degradation Activity

In a baffled triangle flask of 100 mL in capacity, 19 mL of a liquid culture medium (composition: 500 mg/L of 1,4-dioxane, 1 g/L of $K_2HPO_4$, 1 g/L of $(NH_4)_2SO_4$, 50 mg/L of NaCl, 200 mg/L of $MgSO_4.7H_2O$, 10 mg/L of $FeCl_3$, 50 mg/L of $CaCl_2$)) was added, along with 1 mL of a liquid bacterial concentrate of strain N23 (final bacterial concentration: 200 mg-cell/L), after which rotational shaking culture (120 rpm) was performed at 28° C. (n=3). The liquid culture medium was pH-adjusted to pH 3.8, 5.0, 5.9, 7.0, and 8.2 using hydrochloric acid solution and sodium hydroxide solution.

Samples were taken 2.5 hours, 10 hours, and 12 hours after the start of culture, and measured for 1,4-doixane concentration in solution using a headspace gas chromatograph mass spectrometer (GC/MS-QP2010 PLUS, TURBOMATRIX HS40 manufactured by Shimadzu Corporation; hereinafter referred to as "headspace GC/MS"). After confirming linearity in the rate of decrease in 1,4-dioxane concentration over the respective points in time, the 1,4-dioxane degradation rate was calculated. Also, the pH in solution was measured before and after culturing. FIG. 3 shows the relationship of initial pH and degradation rate, while Table 1 shows the pH before and after culturing.

TABLE 1

| Before culturing | 3.8 | 5.0 | 5.9 | 7.0 | 8.2 |
| After culturing | 3.6 | 3.4 | 3.5 | 6.0 | 7.4 |

Strain N23 exhibited the highest 1,4-dioxane degradation rate at pH 7.0. Also, the capability of strain N23 to biodegrade 1,4-dioxane of 500 mg/L in concentration in an acidic environment, was confirmed. Strain N23 was confirmed to maintain degradation activity of 90% or greater at pH 5.9 and 5.0, and 80% or greater at pH 3.8, relative to the degradation activity at pH 7.0.

Also, a drop in pH after culturing was confirmed. This is probably due to a production of glyoxylic acid, which is an intermediate metabolite, through degradation of 1,4-dioxane.

Experiment 2

Biodegradation Treatment of Cyclic Ether by Fed-Batch Process

Example 1

In a liquid tank of 1.2 L in capacity, 0.9 L of simulated wastewater containing 1,4-dioxane was added along with a nutritional supplement (final concentrations of components: 1 g/L of $K_2HPO_4$, 1 g/L of $(NH_4)_2SO_4$, 200 mg/L of $MgSO_4.7H_2O$, 10 mg/L of $FeCl_3$, 50 mg/L of $CaCl_2$), after which strain N23 was added to a bacterial concentration of 970 mg-cell/L and the liquid quantity was adjusted to 1 L.

This wastewater was adjusted to pH 5.0 using a pH controller, and then biodegradation-treated for 24 hours at 30° C. under 1 L/min of aeration. After the 24 hours of biodegradation treatment, the aeration was stopped and the activated sludge containing strain N23 was precipitated, and 0.9 L of supernatant water was discharged. Thereafter, 0.9 L of new simulated wastewater and the nutritional supplement were added, and biodegradation treatment was repeated in the same manner, and this fed-batch process was run for eight days.

Comparative Example 1

A fed-batch process was run in the same manner as in Example 1 above, except that the pH was adjusted to 7.0. (Cyclic Ether Concentrations)

In Example 1 and Comparative Example 1, the 1,4-dioxane concentration in water in the liquid tank was measured with the headspace GC/MS. The measured results of 1,4-dioxane concentrations are shown in FIG. 4.

In both Example 1 and Comparative Example 1, 1,4-dioxane could be degraded in a stable manner by the fed-batch process throughout the experimental period of eight days. In other words, the capability of strain N23 to biodegradation-treat 1,4-dioxane, a cyclic ether, in an acidic environment of pH 5.0, just like in a neutral environment of pH 7.0, was confirmed. Also, in both Example 1 and Comparative Example 1, the bacterial mass increased with each process cycle, resulting in improved processing capability.

Experiment 3

Biodegradation Treatment of Organic Compound

In a flask of 300 mL in capacity, a nutrient salt culture medium (composition: 0.5 g/L of $K_2HPO_4$ and 5 g/L of yeast extract) that has been adjusted to pH 3.6 to 7.9 was added, after which a carbon source was added to 4 g/L, and the liquid quantity was adjusted to 100 mL. Thereafter, strain N23 was added to 70 mg-cell/L, and rotational shaking culture was performed at 28° C. and 120 rpm (n=1). For the carbon source, ethylene glycol, diethylene glycol, and 1,4-butanediol were used. FIG. 5 shows the increases in bacterial concentrations through seven days of culturing.

The capability of strain N23 to grow in an acidic environment of pH 3.0 to 5.0 using ethylene glycol, diethylene glycol, and 1,4-butanediol at a concentration of 4 g/L as carbon sources, was confirmed. Also, strain N23 was confirmed to be able to biodegradation-treat cyclic ethers using the foregoing as carbon sources, because strain N23 is a constitutive 1,4-dioxane-degrading bacterium and constantly producing a degradation enzyme.

What is claimed is:

1. A biodegradation treatment method comprising biodegradation-treating at least one organic compound, to reduce concentration thereof, with strain N23, which is a constitutive 1,4-dioxane-degrading bacterium deposited under Accession No. NITE BP-02032, under a condition of pH 3.8 or higher but no higher than 5.5, which is lower than an optimal pH for 1,4-dioxane degradation activity and growth of the bacterium, while maintaining 80% or greater of degradation activity at pH 7.0 and maintaining the capability of growth,
wherein the organic compound is selected from the group consisting of cyclic ethers, ethylene glycol, diethylene glycol, 1,4-butanediol, and combinations thereof.

2. The biodegradation treatment method according to claim 1, wherein the organic compound is selected from the group consisting of 1,4-dioxane, 1,3-dioxolane, 2-methyl-1,3-dioxolane, tetrahydrofuran, and combinations thereof.

3. The biodegradation treatment method according to claim 1, wherein a carbon source selected from the group consisting of ethylene glycol, diethylene glycol, 1,4-butanediol, 1,4-dioxane, and combinations thereof is added to the organic compound.

4. The biodegradation treatment method according to claim 1, which is performed by a fed-batch process comprising: (i) adding strain N23 to a liquid containing the organic compound, (ii) conducting biodegradation of the organic compound for a given time period, (iii) after step (ii), replacing a part of a supernatant which does not contain strain N23 with a fresh liquid containing the organic compound, and (iv) repeating steps (ii) and (iii) for a given time period.

5. The biodegradation treatment method according to claim 1, which is performed by a continuous process.

6. The biodegradation treatment method according to claim 2, wherein a carbon source selected from the group consisting of ethylene glycol, diethylene glycol, 1,4-butanediol, 1,4-dioxane, and combinations thereof is added to the organic compound.

7. The biodegradation treatment method according to claim 2, which is performed by a fed-batch process comprising: (i) adding strain N23 to a liquid containing the organic compound, (ii) conducting biodegradation of the organic compound for a given time period, (iii) after step (ii), replacing a part of a supernatant which does not contain strain N23 with a fresh liquid containing the organic compound, and (iv) repeating steps (ii) and (iii) for a given time period.

8. The biodegradation treatment method according to claim 2, which is performed by a continuous process.

9. The biodegradation treatment method according to claim 3, which is performed by a fed-batch process comprising: (i) adding strain N23 to a liquid containing the organic compound, (ii) conducting biodegradation of the organic compound for a given time period, (iii) after step (ii), replacing a part of a supernatant which does not contain strain N23 with a fresh liquid containing the organic compound, and (iv) repeating steps (ii) and (iii) for a given time period.

10. The biodegradation treatment method according to claim 3, which is performed by a continuous process.

* * * * *